United States Patent [19]

Ku

[11] Patent Number: 4,659,519
[45] Date of Patent: Apr. 21, 1987

[54] PROCESS FOR SYNTHESIZING ALKYL MONOPEROXYSUCCINIC ACID BLEACHING COMPOSITIONS

[75] Inventor: Hao Ku, Pleasanton, Calif.

[73] Assignee: The Clorox Company, Oakland, Calif.

[21] Appl. No.: 626,826

[22] Filed: Jul. 2, 1984

[51] Int. Cl.$^4$ ............................................. C07C 87/00
[52] U.S. Cl. .............................. 260/502 R; 252/186.26; 252/95; 252/99; 252/102; 8/111
[58] Field of Search ............... 260/406, 413 Q, 502 R

[56] References Cited

U.S. PATENT DOCUMENTS

| | | | |
|---|---|---|---|
| 2,287,064 | 6/1942 | Reichert et al. | 252/186 |
| 3,075,921 | 1/1963 | Brocklehurst et al. | 252/99 |
| 3,143,562 | 8/1964 | Silbert et al. | 260/465 |
| 3,321,512 | 5/1967 | Cooper et al. | 260/502 |
| 3,494,786 | 2/1970 | Nielsen | 117/100 |
| 3,494,787 | 2/1970 | Lund et al. | 117/100 |
| 3,639,285 | 2/1972 | Nielsen | 252/100 |
| 3,655,738 | 4/1972 | Nielsen | 260/502 R |
| 3,770,816 | 11/1973 | Nielsen | 260/502 R |
| 3,819,688 | 6/1974 | Silbert et al. | 260/502 R |
| 3,880,914 | 4/1975 | Nielsen | 260/502 R |

(List continued on next page.)

FOREIGN PATENT DOCUMENTS

| | | |
|---|---|---|
| 635620 | 1/1962 | Canada . |
| 0068547 | 1/1983 | European Pat. Off. . |
| 70067 | 1/1983 | European Pat. Off. . |
| 70066 | 1/1983 | European Pat. Off. . |
| 75419 | 3/1983 | European Pat. Off. . |
| 73541 | 3/1983 | European Pat. Off. . |
| 83560 | 7/1983 | European Pat. Off. . |
| 7109629 | 7/1971 | Netherlands . |

OTHER PUBLICATIONS

A. Ault, Techniques and Experiments for Organic Chemistry, 2nd Ed., 1976, pp. 19-28.
S. N. Lewis, "Peracid and Peroxide Oxidations," in: Oxidation, 1969, pp. 213-258.

K. Balenovic et al, "Asymmetric Synthesis of Sulphoxides with α-Substituted Monoperglutaric Acids," Chemistry and Industry, Apr. 15, 1961, pp. 469-470.

(List continued on next page.)

Primary Examiner—Paul Lieberman
Assistant Examiner—John F. McNally
Attorney, Agent, or Firm—Joel J. Hayashida; Stephen M. Westbrook

[57] ABSTRACT

The invention relates to a novel process for synthesizing surface active peroxyacid bleaching agents and compositions which are named α or β alkyl monoperoxysuccinic acids and have the general structure

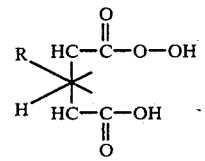

wherein R is an unsubstituted or substituted straight chain alkyl of 6 to 16 carbon atoms, unsubstituted or substituted branched chain alkyl of 6 to 20 carbon atoms, or a phenyl group substituted with one or more of H, alkyl of 1 to 14 carbon atoms, F, Cl, $NO_3$, $OSO_3M$, $SO_3M$, or $COOM$, and M is further defined as H, an alkali metal or ammonium cation.

The invention provides a novel process for synthesizing these alkyl monoperoxysuccinic acids which is relatively inexpensive, high yielding, and safe.

The bleaching compositions are useful for bleaching fabrics and other laundering purposes. The bleaching compositions of the invention may also contain peroxyacid stabilizers, builders, fillers, and surfactants.

14 Claims, 3 Drawing Figures

U.S. PATENT DOCUMENTS

| | | | |
|---|---|---|---|
| 3,956,159 | 5/1976 | Jones | 252/104 |
| 3,975,280 | 8/1976 | Hachmann et al. | 252/102 |
| 4,006,029 | 2/1977 | Guile et al. | 106/58 |
| 4,013,575 | 3/1977 | Castrantas et al. | 252/104 |
| 4,085,133 | 4/1978 | Briody | 260/502 R |
| 4,088,676 | 5/1978 | Hofen et al. | 260/502 R |
| 4,091,544 | 5/1978 | Hutchins | 34/9 |
| 4,100,095 | 7/1978 | Hutchins et al. | 252/99 |
| 4,119,660 | 10/1978 | Hutchins | 260/502 R |
| 4,126,573 | 11/1978 | Johnston | 252/99 |
| 4,170,453 | 10/1979 | Kitko | 8/111 |
| 4,172,086 | 10/1979 | Berkowitz | 260/406 |
| 4,233,235 | 11/1980 | Camden et al. | 260/502 R |
| 4,244,884 | 1/1981 | Hutchins et al. | 260/502 R |
| 4,259,201 | 3/1981 | Cockrell, Jr. et al. | 252/103 |
| 4,287,135 | 9/1981 | Stober et al. | 260/502 R |
| 4,314,949 | 2/1982 | Bettie, III et al. | 260/502 R |
| 4,337,213 | 6/1982 | Marynowski et al. | 260/502 R |
| 4,370,251 | 1/1983 | Liao et al. | 42/186.42 |
| 4,374,035 | 2/1983 | Bossu | 252/191 |
| 4,385,008 | 5/1983 | Hignett | 260/502 |
| 4,391,723 | 7/1983 | Bacon et al. | 252/90 |
| 4,391,724 | 7/1983 | Bacon | 252/90 |
| 4,391,725 | 7/1983 | Bossu | 252/90 |
| 4,443,352 | 4/1984 | Broze et al. | 252/94 |

OTHER PUBLICATIONS

M. F. Hawthorne et al, "A Re-Examination of the Peroxyacid Cleavage of Ketones. II. Kinetics of Baeyer–Villiger Reaction," *J.A.C.S.*, vol. 80, pp. 6398–6404, (1958).

M. F. Hawthorne et al, "A Re-Examination of the Peroxyacid Cleavage of Ketones. I. Relative Migratory Aptitudes," *J.A.C.S.*, vol. 80, pp. 6393–6398, (1958).

W. E. Parker et al, "Peroxides. IV. Aliphatic Diperacids," *J.A.C.S.*, vol. 79, pp. 1929–1931, (1957).

D. Swern et al, "Peroxides. III. Structure of Aliphatic Peracids . . . Etc.," J.A.C.S., vol. 77, pp. 5537–5541, (1955).

W. D. Emmons et al, "Peroxytrifluoroacetic Acid. III. The Hydroxylation of Olefins," J.A.C.S., vol. 76, pp. 3472–3474, (1954).

W. D. Emmons, "Peroxytrifluoroacetic Acid. II. The Oxidation of Anilines to Nitro-Benzenes," vol. 76, pp. 3470–3472, (1954).

W. D. Emmons, Peroxytrifluoroacetic Acid. I. The Oxidation of Nitrosamines to Nitramines," J.A.C.S., vol. 76, pp. 3468–3470, (1954).

D. Swern, Organic Peroxides, vol. 1, p. 405, (1970).

α or β-Decyl Monoperoxysuccinic Acid (MPSA) vs. Decyl Butane Diperoxoic Acid (DBDA)

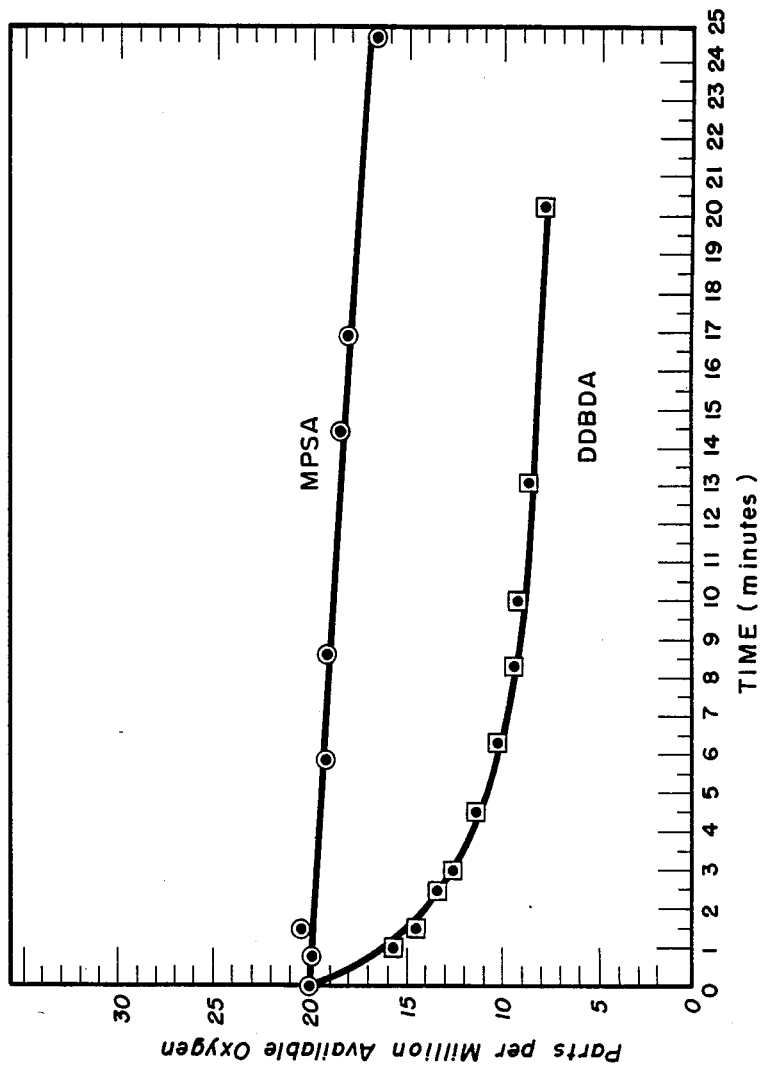

PROCESS FOR SYNTHESIZING ALKYL MONOPEROXYSUCCINIC ACID BLEACHING COMPOSITIONS

TECHNICAL FIELD

The invention relates to surface active peroxyacids which are useful as bleaching compositions.

BACKGROUND OF THE INVENTION

Recently, manufacturers have been developing peroxyacid (also denoted as "peracid") bleaching agents. Efforts have been made to identify and obtain further peroxyacid bleaching agents which can effectively oxidize stains.

SUMMARY OF THE INVENTION

This invention provides novel surface active peroxyacid bleaching agents comprising peroxyacids of the general structure:

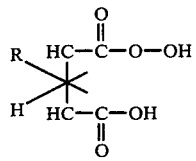

wherein R is a substituted or unsubstituted straight chain alkyl of 6 to 16 carbon atoms, substituted or unsubstituted branched chain alkyl of 6 to 20 carbon atoms, or a phenyl group which is substituted with one or more of H, alkyl of 1 to 14 carbon atoms, F, Cl, $NO_3$, $OSO_3M$, $SO_3M$, or COOM, and wherein M is further defined as H, an alkali metal or ammonium cation.

These particular compounds may also be called α or β-alkyl monoperoxysuccinic acids.

The invention further provides a bleaching composition comprising the above peroxyacid in combination with a stabilizer selected from hydrated aluminum salts, hydrated magnesium salts, carboxylic acids and boric acid. Bleaching compositions of this sort can also contain fillers, builders, and surfactants.

The invention still further provides a method of bleaching fabrics comprising contacting fabrics with the foregoing bleaching compositions.

The invention also provides a novel process for preparing these α or β alkyl monoperoxysuccinic acids comprising:

(a) combining:
 (i) an alkyl succinic anhydride;
 (ii) a water immiscible solvent;
 (iii) a water soluble solvent; and
 (iv) hydrogen peroxide; and
(b) agitating under heat.

The invention thus provides both novel peroxyacid compositions and a new, relatively inexpensive, high yielding, safe process for producing these compositions.

BRIEF DESCRIPTION OF THE DRAWINGS

FIG. 3 is a graphical depiction of the decay kinetics of dodecyl monoperoxysuccinic acid and dodecyl butane diperoxic acid.

DETAILED DESCRIPTION OF THE INVENTION

Figure 1:
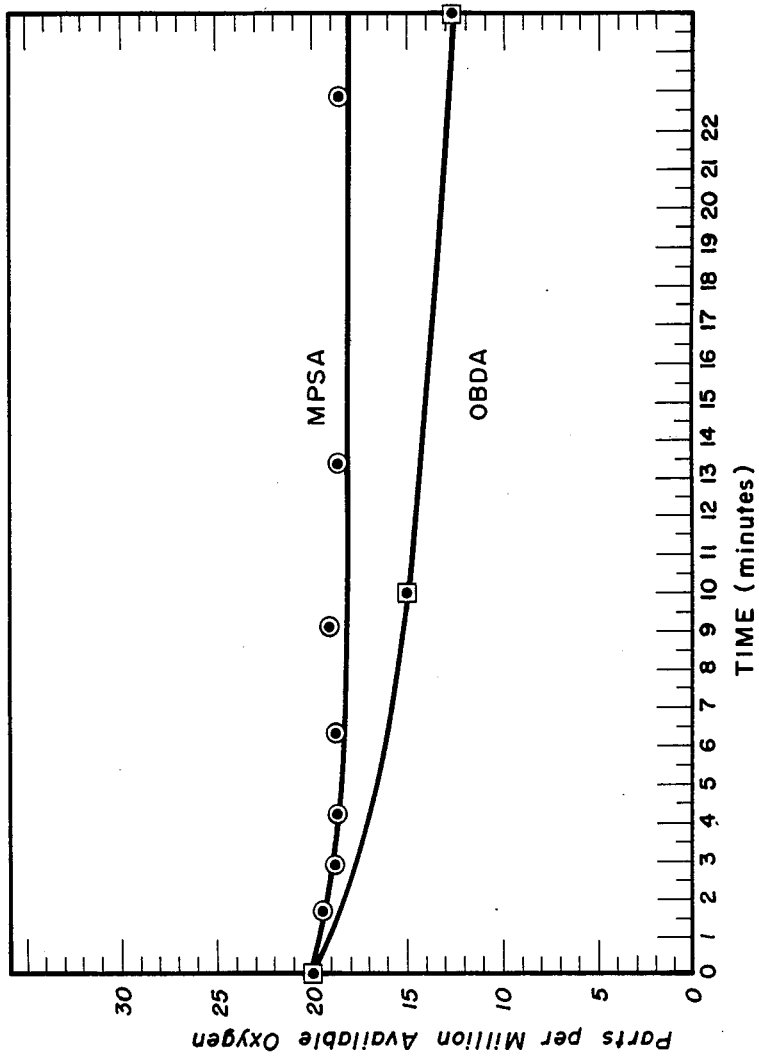
FIG. 1 is a graphical depiction of the decay kinetics of octyl monoperoxysuccinic acid and octyl butane diperoxic acid.

It has been surprisingly discovered that α or β alkyl monoperoxysuccinic acids and their derivatives are effective bleaching agents. These particular compounds had not been heretofore synthesized. These novel bleaching agents have now been prepared, and the process of synthesizing them is disclosed as set forth below.

α OR β ALKYL MONOPEROXYSUCCINIC ACIDS

These surface active alkyl monoperoxysuccinic acid bleaching agents have the general structure:

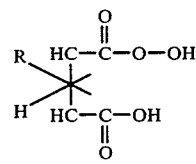

wherein R, is a substituted or unsubstituted straight chain alkyl of 6 to 16 carbon atoms, substituted or unsubstituted branched chain alkyl of 6 to 20 carbon atoms, or a phenyl group which is substituted with one or more of H, alkyl of 1 to 14 carbon atoms, F, Cl, $NO_3$, $OSO_3M$, $SO_3M$, or COOM, and wherein M is further defined as H, an alkali metal or ammonium cation.

Particular examples of the straight chain α or β alkyl monoperoxysuccinic acids which have been synthesized include the octyl, decyl, and dodecyl monoperoxysuccinic acids, whose structures are set forth below:

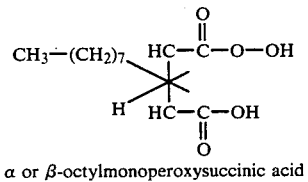

α or β-octylmonoperoxysuccinic acid

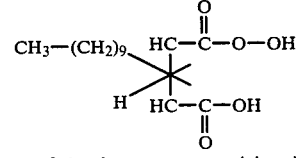

α or β-decylmonoperoxysuccinic acid

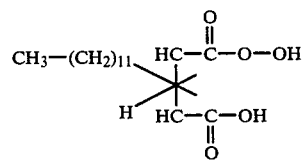

α or β-dodecylmonoperoxysuccinic acid

PROCESS FOR SYNTHESIZING

Substituted, non-surface active peroxyacids (also denoted as peracids) have been synthesized by combining a source of hydrogen peroxide with an anhydride in the presence of an organic, polar solvent, such as methylene chloride. See, S. N. Lewis, "Peracid and Peroxide Oxidations," *Oxidation,* Volume 1, p. 217 (1969). These systems do not experience the problems that are encountered when one tries to make surface active peracids.

Other systems at present which vary the standard process include, for example, Camden et al, U.S. Pat. No. 4,233,235, which discloses a continuous process for making aliphatic diperoxyacids in which a strong acid, sulfuric acid is added to an aliphatic carboxylic acid mixture. Unfortunately, this particular system appears to generate large amounts of heat, and to require relatively expensive processing equipment.

Still other references have proposed other types of solvents. However, none of the references appeared to have disclosed how to synthesize surface active monoperoxysuccinic acids. Further, nothing in the prior art discloses a process for making relatively pure surface active monoperoxysuccinic acids.

The surface active monoperoxysuccinic acids of this invention are believed to be advantageous over other peroxy acids, for instance, the alkyl butane diperoxoic acids, which are somewhat similar compounds, but which have two peroxo moieties.

As disclosed herein, the novel process comprises:
(a) combining:
 (i) an alkyl succinic anhydride;
 (ii) a water immiscible solvent;
 (iii) a water soluble solvent; and
 (iv) hydrogen peroxide; and
(b) agitating under heat.

The alkyl succinic anhydride starting materials of the inventive process have the general structure:

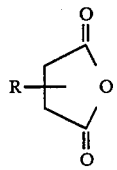

wherein R is an alkyl group of 6 to 20 carbon atoms.

The R group on these anhydrides may be appropriately substituted, as defined above, for FIG. 4, to include branched chain alkyls, water solubilizing groups, e.g., SO$_3$H, etc., so as to form the peroxyacids discussed and depicted herein above.

The water immiscible solvents used herein include halogenated, i.e., chlorinated, fluorinated or chlorofluorinated alkyls of 1 to 6 carbon atoms and unsubstituted and halogenated aromatic hydrocarbons of 6 to 12 carbon atoms.

Representative halogenated alkyls include methylene chloride (dichloromethane) and carbon tetrachloride (tetrachloromethane). Representative aromatic hydrocarbons include toluene, dichlorobenzene, etc. Methylene chloride is especially preferred as the water immiscible solvent.

The water soluble solvent used herein includes straight chain, branched chain, and substituted alcohols of 1 to 6 carbon atoms; straight chain, branched chain and substituted glycols of 1 to 6 carbon atoms, and straight chain, branched chain, and substituted glycol ethers of 1 to 6 carbon atoms. Still other candidates include esters of 1 to 10 carbon atoms and ketones of 1 to 6 carbon atoms. Yet other possible solvents include such diverse solvents as dioxane, acetonitrile, dimethylformamide (DMF) and tetrahydrofuran (THF).

Synthesis of the desired monoperoxysuccinic acids require water soluble solvents. In practice, it has been discovered that these solvents carry the hydrogen peroxide into the nonaqueous phase of the alkylsuccinic anhydride/immiscible solvent mixture. The preferred water soluble solvent is an alcohol of 1 to 6 carbon atoms. One particularly preferred alcohol is ethyl alcohol or ethanol.

It is preferable that neither the water immiscible solvent nor the water soluble solvent react with either the peroxyacid or H$_2$O$_2$ in situ. The apparent preference for such selectively non-reactive solvents is based on preventing an early decomposition of the peroxy compound formed in the reaction medium.

Further, the preferred volume ratios of the water immiscible solvent to water soluble solvent is at least 2:1, more preferably about 5:1 to about 10:1.

The hydrogen peroxide used can vary in purity from 50–99.9%. The amount of hydrogen peroxide used must be in excess of the anhydride. Preferably, the molar ratio of hydrogen peroxide to anhydride will be at least 2:1, and, most preferably, about 4:1.

The reaction conditions under which the process takes place include agitation of the mixture and heating. An example of this is a refluxing reaction, wherein temperatures of preferably about 35° to 45° C., most preferably about 42° C., for about 3 to 4 hours, are used, if methylene chloride is the immiscible solvent.

The end product, $\alpha$ or $\beta$ alkyl monoperoxysuccinic acid is obtained by removing all solvent, e.g., by air drying, vacuum drying under reduced pressure, etc. Alternatively, recrystallization techniques could be used, such as shown in A. Ault, *Techniques and Experiments for Organic Chemistry,* 2d Ed., pages 19–28, 1976, which are incorporated herein by reference.

For purposes of further exemplification, although the applicant does not intend to be solely limited thereto, the method of preparing the novel compositions of this invention are illustrated below in EXPERIMENTAL.

EXPERIMENTAL

EXAMPLE I

Synthesis of $\alpha$ or $\beta$-Dodecyl Monoperoxysuccinic Acid

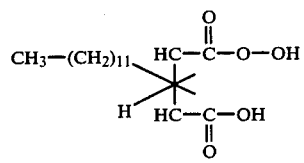

0.480 ml 70% hydrogen peroxide (10 m moles) and 4 ml anhydrous ethanol is placed in a 3-necked 100 ml round-bottomed flask fitted with a reflux condenser, a mechanical stirrer, and a 50 ml dropping funnel. The flask is surrounded by a water bath. The bath temperature is maintained at around 60° C. After the mixture has been vigorously stirred for 2 minutes, a solution of 1.34 g (5.0 m moles) of dodecyl succinic anhydride (Humphrey Chemical Co., recrystallized from hexane, m.p. 73°–74° C.) in 20 ml methylenechloride is added from the dropping funnel at such a rate that a moderate reflux is maintained. After the addition has been completed, an additional 0.480 ml 70% hydrogen peroxide is added in one portion and the mixture is refluxed with continuous vigorous stirring for an additional 3.5 hours.

The reaction mixture is then transferred to a 70×5 mm crystallizing dish. The solvents are removed by evaporating in a hood. After being air-dried overnight, a yield of 1.5 g of product, which is about 99% with respect to starting materials, is obtained. Alternatively, product may be obtained by removing solvent under reduced pressure and vacuum drying. A standard potassium iodide-thiosulfate titration, performed as shown in S. N. Lewis, "Peracid and Peroxide Oxidations," in *Oxidation*, Vol. 1, pp 221-22 (1969), which pages are incorporated herein by reference, showed 3.42% (5.03% theoretical) active oxygen. The structure of this product was assigned as a mixture of α and β-octyl monoperoxysuccinic acid on the basis of the following spectral data: IR (Nujol mull) 1750 cm$^{-1}$, 1710 cm$^{-1}$, $^{13}$C-NMR (CD$_2$Cl$_2$, 90 MHZ): α-isomer, PPM, 176.0, 177.3, 14-41 (C-aliphatic); β-isomer, PPM, 172.9, 180.3, 14-41 (C-aliphatic).

EXAMPLE II

Synthesis of α or β-Octyl monoperoxysuccinic acid

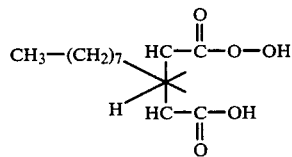

α or β-octyl monoperoxysuccinic acid may be prepared according to the procedure of Example I, above. In place of the dodecyl succinic anhydride (5 m moles), octyl succinic anhydride (5 m moles) is used. The yield for the reaction product, as calculated from the available oxygen, is 50%, using a standard potassium iodide-thiosulfate titration as in Example I, above.

EXAMPLE III

Synthesis of α or β-Decyl monoperoxysuccinic acid

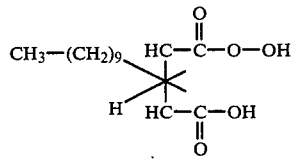

α or β-decyl monoperoxysuccinic acid may be prepared according to the procedure in Example I, above, by substituting decyl succinic anhydride (5 m moles) for the dodecyl succinic anhydride (5 m moles). Utilizing this procedure, the yield was 52% as calculated from the available oxygen, as shown in Examples I and II.

The preceding procedures have been successfully scaled up using larger amounts of the selected anhydride.

The applicants believe the procedures utilized are responsible for the high yields of peroxyacids produced.

The above procedure comprises a safe, rapid and efficient process in which good yields of the desired α or β alkyl monoperoxysuccinic acids are obtained. Advantages of the present invention are that the reaction is performed in a rapid, safe and easily controlled operation. The high heats of reaction, and expensive materials which were utilized in previous methods are avoided. As shown in the next section of the instant application, these alkyl monoperoxysuccinic acids are suitable for use as bleaching compositions.

BLEACHING COMPOSITIONS

For fabric, textile or even hard surface bleaching purposes, at least 1 part per million active oxygen (p.p.m. A.O.) in the wash water or 1% by weight of the surface active peroxyacid itself in the composition should be present. The range of the amount of peroxyacid in solution should be about 1 to 30 p.p.m. A.O., or 1 to 30% by weight of the composition. Preferably, the amount of peroxyacid is about 5 to 20% by weight of the composition.

Additionally, however, the surface active peroxyacids of the invention can be combined with various cleaning adjuncts, to form bleaching compositions. One particular example is a bleaching composition comprising:

(a) A peroxyacid of the general structure

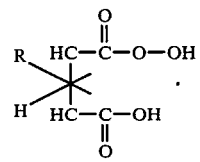

wherein R is a substituted or unsubstituted straight chain alkyl of 6 to 16 carbon atoms, substituted or unsubstituted branched chain alkyl of 6 to 20 carbon atoms, or a phenyl group which is substituted with one or more of H, alkyl of 1 to 14 carbon atoms, F, Cl, NO$_3$, OSO$_3$M, SO$_3$M, or COOM, and wherein M is further defined as H, an alkali metal or ammonium cation; and (b) a stabilizer selected from:

hydrated aluminum salts, hydrated magnesium salts, carboxylic acids and boric acid.

Examples of these particular stabilizers can include potassium aluminum sulfate dodecahydrate, magnesium sulfate heptahydrate, sodium aluminum sulfate dodecahydrate, magnesium ammonium sulfate hexahydrate, etc. Particular acid stabilizers besides boric acid include maleic acid, succinic acid, substituted-succinic acids, azelaic acid, dodecanedioic acid, cyclohexane dicarboxylic acid. However, boric acid is particularly preferred as a stabilizer to prevent violent exothermic decomposition of this particular composition.

These particular bleaching compositions may also comprise a filler selected from alkali metal and ammonium salts of sulfates, for example, sodium sulfate, ammonium sulfate and potassium sulfate. Other fillers are the alkali metal and ammonium salts of carbonates, bicarbonates, acetates and silicates. These fillers have the purposes of "bulking" the product to provide a composition which is easily measured by the consumer.

Further, a builder may be added which can be selected from the alkali metal salts of carbonates, borates, polyphosphates, phosphates, zeolites, silicates; nitrilotriacetic acid and its alkali metal salts; and ethylene diamine tetraacetic acid and its alkali metal salts. Particularly preferred as builders are such compounds as sodium carbonate, sodium tripolyphosphate, and nitrilotriacetic acid (NTA).

Also, particular laundry bleaching composition additives include surfactants selected from anionic, nonionic, amphoteric, cationic, and zwitterionic surfactants.

Anionic surfactants suitable for use in this invention include the alkali metal and ammonium salts of fatty acids, having about 8-20 carbon atoms in their chain lengths; substituted and unsubstituted alkyl sulfates; substituted and unsubstituted alkyl sulfonates; substituted and unsubstituted alkyl benzene sulfonates (examples of which include both "HLAS", for alkyl benzene sulfonic acid, and "LAS", for linear alkyl benzene sulfonate, sodium salt).

Still other suitable anionic surfactants include anionic aminocarboxylates, such as N-acyl-sarcosinates, alkyl, aryl, and alkylaryl sarcosinates; alpha-olefin sulfonates; sulfates of natural fats and oils (e.g., castor, coconut, tallow oils); sulfated esters; ethoxylated and sulfated alkylphenols; ethoxylated and sulfated alcohols (also known as alkyl ether sulfates) and phosphated esters which are generally phosphorylated nonionics such as ethoxylated alcohols, ethoxylated alkylphenols, and polyoxythylene-polyoxypropylene block co-polymers.

Suitable nonionic surfactants include polyoxyethylenes, polyoxypropylenes; alkylpolyoxyethylenes; alkylarylpolyoxyethylenes; ethoxylated alkylphenols; carboxylic acid esters such as glycerol esters of fatty acids, certain polyethylene glycol esters, anhydrosorbitol esters, ethoxylated anhydrosorbital esters, ethylene and methylene glycol esters, propanediol esters, and ethoxylated natural fats and oils (e.g., tallow oils, coco oils, etc.); carboxylic amides such as 1:1 amine acid diethanolamine condensates, 2:1 amine/acid diethanolamide condensates, and monoalkanolamine condensates such as ethanolamine condensates, and isopropanolamine condensates, polyoxyethylene fatty acid amides; certain polyalkylene oxide block co-polymers such as polyoxypropylene-polyoxyethylene block co-polymers; and other miscellaneous nonionic surfactants such as organosilicones.

Suitable cationic surfactants include a wide range of classes of compounds, including non-oxygen-containing alkyl mono-, di- and polyamines, and resin derived amines; substituted alkyl, alkylol imidazolines, such as 2-alkyl-1-(hydroxyethyl)-2-imidazolines; amide linked amines, and quaternary ammonium salts ("quats").

Further, suitable amphoteric surfactants containing both acidic and basic hydrophilic moieties in their structure, include oxygen-containing amines, such as amine oxides (which appear to act as cationics in acidic solutions, and as nonionics in neutral or alkaline solutions); polyoxyethylene alkyl and alicyclic amines; alkyl betaines, amino-carboxylic acids and salts thereof, amino-carboxylic acid esters, and others.

Further examples of anionic, nonionic, cationic and amphoteric surfactants which may be suitable for use in this invention are depicted in Kirk-Othmer, *Encyclopedia of Chemical Technology*, Third Edition, Vol. 22, pages 347-387, and *McCutcheon's Detergents and Emulsifiers*, North American Edition, 1983, which are incorporated herein by reference.

Zwitterionic surfactants which may be suitable for use in the compositions of this invention may be broadly described as derivatives of secondary and tertiary amines, derivatives of heterocyclic secondary and tertiary amines, or derivatives of quaternary ammonium, quaternary phosphonium or tertiary sulfonium compounds. Suitable examples of these zwitterionic surfactants can be found described in Jones, U.S. Pat. No. 4,005,029, Columns 11-15, which are incorporated herein by reference.

The particular surface active peroxyacid bleaches provided in this invention have been found to be particularly effective against various stains. For example, comparison of TABLE I below shows the following:

TABLE I

| WASH WATER COMPOSITIONS | % SRE[1] GRASS |
| --- | --- |
| Tide ®[2] | 87.58 |
| Octyl MPSA[3] 20 ppm A.O. | 91.60 |
| Decyl MPSA[4] 20 ppm A.O. | 93.44 |
| Dodecyl MPSA[5] 20 ppm A.O. | 94.79 |

[1]% SRE Grass: this is the percent stain removal of grass stains as measured spectrophotometrically. Higher values indicate better performance.
[2]Tide ®: is a registered trademark of Procter & Gamble Co. for laundry detergent. 1.5 grams/l was present in all examples shown in this Table.
[3]Octyl MPSA: this is an α or β monoperoxysuccinic acid having 8 carbons in the alkyl chain.
[4]Decyl MPSA: this is an α or β monoperoxysuccinic acid having 10 carbons in the alkyl chain.
[5]Dodecyl MPSA: this is an α or β monoperoxysuccinic acid having 12 carbons in the alkyl chain.

Further advantages of these peroxyacids are their relative stability in aqueous solution *near* their pKa's. It is generally agreed that for peroxyacids, pKa's are around 8.5-9.5. Within this range, optimal bleaching is obtained. Since most American washing machines and laundries operate at pH's of around 8-10, this is also the particular range for favorable peroxyacid usage. However, the benefit of obtaining the optimal activity of surface active peroxyacids at these particular pH's also has the disadvantage of decreasing their stability.

Figure 2:
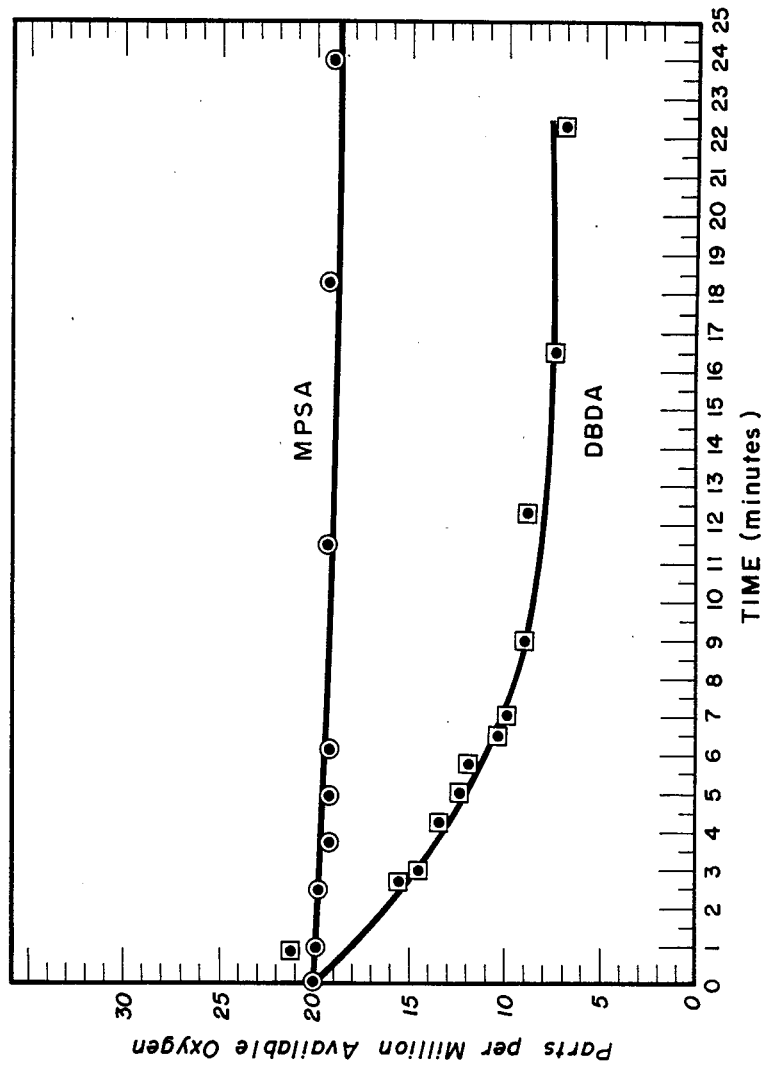
FIG. 2 is a graphical depiction of the decay kinetics of decyl monoperoxysuccinic acid and decyl butane diperoxic acid.

Surprisingly, however, the alkyl monoperoxysuccinic acids have increased stability in aqueous solution at the optimal pH's. Alkyl monoperoxysuccinic acids were dissolved in water, compared against somewhat similar compositions, namely, alkyl butane diperoxoic acids, and found to have greater stability than these alkyl butane diperoxoic acids. These are shown in the three illustrations, FIGS. 1-3. FIG. 1 compares the octyl monoperoxysuccinic acid vs. the octyl butane diperoxoic acid. FIG. 2 compares the decyl monoperoxysuccinic acid vs. the decyl butane diperoxoic acid. FIG. 3 compares the dodecyl monoperoxysuccinic acid vs. dodecyl butane diperoxoic acid. All of these trials were run in a buffered solution at a pH range of 8.3-9.0 at about 100° F. (37.7° C.), without additional water hardness, and with a surfactant, or a mixture of surfactants such as is found in Tide ® laundry detergent (registered trademark of Procter & Gamble) which includes a mixture of sodium alkyl sulfate, sodium alkyl ether sulfate, and sodium alkyl benzene sulfonate. Comparison of these figures shows that the alkyl monoperoxysuccinic acids have much greater stability and longer half lives than the corresponding alkyl butane diperoxoic acids.

The foregoing examples and embodiments are solely for the purposes of illustration and not intended to restrict in any manner the scope of this invention. The invention is further disclosed and illustrated by reference to the claims hereto.

What is claimed is:

1. A process for synthesizing the monoperoxyacid having the general structure:

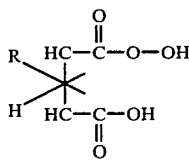

wherein R is an unsubstituted or substituted straight chain alkyl of 6 to 16 carbon atoms, unsubstituted or substituted branched chain alkyl of 6 to 20 carbon atoms, or a phenyl group substituted with one or more of H, alkyl of 1 to 14 carbon atoms, F, Cl, $NO_3$, $OSO_3M$, or COOM, and M is further defined as H, an alkali metal or ammonium cation, said process comprising:

(a) combining:
  (i) an alkylsuccinic anhydride of the general structure:

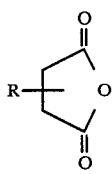

wherein R is defined as above;
  (ii) a water immiscible organic solvent;
  (iii) a water soluble organic solvent, said water immiscible organic solvent being in a ratio with said water soluble organic solvent of at least 2:1; and
  (iv) hydrogen peroxide, said hydrogen peroxide being in a ratio with said anhydride in a ratio of at least 2:1; and
(b) agitating under heat; said process producing substantially no diperoxy acid.

2. The process of claim 1 wherein neither said water immiscible solvent nor said water soluble solvent reacts with either hydrogen peroxide or peroxyacid.

3. The process of claim 2 wherein the water immiscible solvent is selected from:
  chlorinated, fluorinated or chlorofluorinated alkyls of 1 to 5 carbon atoms; and unsubstituted or halogenated aromatic hydrocarbons of 6–12 carbon atoms.

4. The process of claim 3 wherein said water soluble organic solvent is selected from:
  straight chain, branched chain and substituted alcohols of 1 to 6 carbon atoms; straight chain, branched chain and substituted glycols of 1 to 6 carbon atoms, straight chain, branched and substituted glycol ethers of 1 to 6 carbon atoms; esters of 1 to 10 carbon atoms; ketones of 1 to 6 carbon atoms; dioxane; acetonitrile; dimethyl formamide; and tetrahydrofuran.

5. The process of claim 3 wherein said water immiscible solvent is methylene chloride.

6. The process of claim 5 wherein said water soluble solvent is a straight chain alcohol of 1 to 6 carbon atoms.

7. The process of claim 6 wherein the ratio of alcohol to methylene chloride is about 1:10.

8. The process of claim 7 wherein the amount of hydrogen peroxide must exceed the amount of anhydride in a molar ratio of at least 2:1.

9. The process of claim 8 wherein step (b) comprises a refluxing reaction.

10. The process of claim 1 further comprising (c) removing said solvents.

11. A process for synthesizing the monoperoxyacid

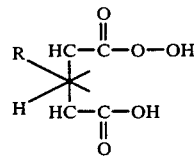

wherein R is an unsubstituted or substituted straight chain alkyl of 6 to 16 carbon atoms, substituted or unsubstituted branched chain alkyl of 6 to 20 carbon atoms, or a phenyl group substituted with one or more of H, alkyl 1 to 14 carbon atoms, F, Cl, $NO_3$, metal or ammonium cation, the process comprising:

(a) combining:
  (i) an alkyl-substituted succinic anhydride;
  (ii) a water immiscible organic solvent;
  (iii) hydrogen peroxide; and
  (iv) a water soluble organic solvent to carry the hydrogen peroxide into solution; and
(b) refluxing the combination;
said water immiscible organic solvent and said water soluble organic solvent being in a ratio of at least 2:1; said hydrogen peroxide and said anhydride being in a ratio of at least 2:1; and said process producing substantially no diperoxy acid.

12. The process of claim 11 wherein the compound synthesized has the structure:

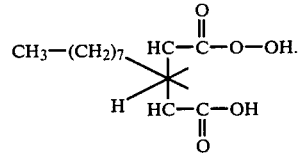

13. The process of claim 11 wherein the compound synthesized has the structure:

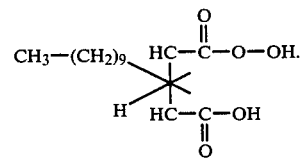

14. The process of claim 11 wherein the compound synthesized has the structure:

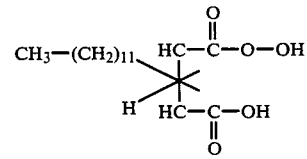

* * * * *